United States Patent
Ni et al.

(10) Patent No.: US 10,927,051 B2
(45) Date of Patent: Feb. 23, 2021

(54) METHOD FOR PREPARING AROMATIC HYDROCARBONS

(71) Applicant: Dalian Institute of Chemical Physics, Chinese Academy of Sciences, Dalian (CN)

(72) Inventors: Youming Ni, Dalian (CN); Wenliang Zhu, Dalian (CN); Zhongmin Liu, Dalian (CN); Zhiyang Chen, Dalian (CN); Yong Liu, Dalian (CN); Hongchao Liu, Dalian (CN); Xiangang Ma, Dalian (CN); Shiping Liu, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 0 days.

(21) Appl. No.: 16/344,375

(22) PCT Filed: Aug. 22, 2017

(86) PCT No.: PCT/CN2017/098510
§ 371 (c)(1),
(2) Date: Apr. 24, 2019

(87) PCT Pub. No.: WO2018/076910
PCT Pub. Date: May 3, 2018

(65) Prior Publication Data
US 2019/0256440 A1  Aug. 22, 2019

(30) Foreign Application Priority Data
Oct. 24, 2016  (CN) .......................... 201610985085.2

(51) Int. Cl.
*C07C 1/22* (2006.01)
*B01J 29/40* (2006.01)
*C07C 1/20* (2006.01)

(52) U.S. Cl.
CPC ................. *C07C 1/22* (2013.01); *B01J 29/40* (2013.01); *C07C 1/20* (2013.01); *C07C 2529/40* (2013.01); *Y02P 20/52* (2015.11); *Y02P 20/584* (2015.11)

(58) Field of Classification Search
CPC ......... C07C 1/20; C07C 1/22; C07C 2529/40; C07C 15/02; C07C 15/04; C07C 15/06; C07C 15/08; B01J 29/40; B01J 29/90; B01J 38/14; Y02P 20/52; Y02P 20/584
See application file for complete search history.

(56) References Cited

U.S. PATENT DOCUMENTS

| | | | | |
|---|---|---|---|---|
| 3,894,107 A | * | 7/1975 | Butter | ...................... B01J 29/18 585/408 |
| 3,931,349 A | * | 1/1976 | Kuo | .......................... C10L 1/06 585/310 |
| 4,046,825 A | * | 9/1977 | Owen | ...................... C07C 1/20 585/408 |
| 4,590,321 A | | 5/1986 | Chu et al. | |
| 4,686,312 A | | 8/1987 | Chu et al. | |
| 2016/0090332 A1 | | 3/2016 | Buchanan et al. | |

FOREIGN PATENT DOCUMENTS

| | | |
|---|---|---|
| CN | 101016475 A | 8/2007 |
| CN | 103058807 A | 4/2013 |
| CN | 103288582 A | 9/2013 |
| CN | 104326859 A | 2/2015 |
| CN | 106518591 A | 3/2017 |

OTHER PUBLICATIONS

Wu, Xiangguo, "First Search, Application No. 2016109850852", dated Apr. 11, 2019, State Intellectual Property Office.

* cited by examiner

*Primary Examiner* — Youngsul Jeong
*Assistant Examiner* — Jason Y Chong
(74) *Attorney, Agent, or Firm* — Edwin A. Sisson, Attorney at Law, LLC; Jeffrey J. Banyas

(57) ABSTRACT

Disclosed is a method for preparing aromatic hydrocarbons, particularly relates to the preparation of the aromatic hydrocarbons by passing methanol and carbon monoxide through a reactor loaded with an acidic ZSM-5 molecular sieve catalyst containing no metal additive under reaction conditions. Compared with the prior art, the method provided by the present invention can improve and stabilize the selectivity to aromatic hydrocarbons, particularly BTX, by adding carbon monoxide in methanol aromatization, and also prolongs the single-pass life of the catalyst. The performance of an inactivated catalyst is not significantly degraded after repeated regenerations. Furthermore, the catalyst preparation process omits the step of adding a metal additive, so that not only the process is simplified, but also costs are greatly reduced, and environmental protection is facilitated.

7 Claims, No Drawings

METHOD FOR PREPARING AROMATIC HYDROCARBONS

PRIORITIES AND CROSS REFERENCES

This Application claims priority from International Application No. PCT/CN2017/098510 filed on 22 Aug. 2017 and Chinese Application No. 201610985085.2 filed on 24 Oct. 2016, the teachings of each of which are incorporated herein by reference in their entirety.

TECHNICAL FIELD

The present invention relates to a method for preparing aromatic hydrocarbons, particularly to the preparation of the aromatic hydrocarbons by passing methanol and carbon monoxide through a catalyst loaded with an acidic ZSM-5 molecular sieve containing no metal additive.

BACKGROUND

Aromatic hydrocarbons, especially benzene, toluene and xylene, collectively known as BTX, are important organic chemical raw materials with a yield and scale second only to ethylene and propylene. The derivatives of aromatic hydrocarbons are widely used in chemical products and fine chemical products such as fuels, petrochemicals, chemical fibers, plastics and rubbers.

At present, aromatic hydrocarbons are mainly produced from petroleum, wherein 70% of BTX aromatic hydrocarbons in the world come from a catalytic reforming process unit of a refinery. The catalytic reforming technology is a process type using naphtha as a raw material, in which semi-regeneration and continuous-regeneration reforming are employed. The catalytic reforming generally employs a platinum-containing catalyst. Typical processes for the catalytic reforming are represented by UOP's CCR platformer process and IFP's Aromizer process. In addition, the production process of aromatic hydrocarbons based on petroleum route further comprises gasoline hydrogenation technology, aromatic hydrocarbons extraction technology, heavy aromatic hydrocarbons lightening technology, and light hydrocarbons aromatization technology.

With the continuous development of society, the demand for aromatic hydrocarbons in the world is increasing. However, the increasingly short petroleum resources cause the prices of aromatic hydrocarbons, especially BTX, to remain high. In view of the current energy structure of "rich in coal and poor in petroleum" in China, it is of great significance to vigorously develop a coal chemical route to produce aromatic hydrocarbons. In the technology for producing aromatic hydrocarbons in coal chemical industry, the study on the technology of methanol, which is a platform product in coal chemical industry, to aromatic hydrocarbons (MTA) is the most extensive. The technology of methanol to aromatic hydrocarbons generally employs an acidic ZSM-5 molecular sieve catalyst modified by a metal additive of zinc, gallium, silver, etc. However, the factors such as the ease of sublimating or aggregating for metals under high temperature conditions, the rapid decrease in selectivity to aromatic hydrocarbons, the short life of catalyst, the low selectivity to BTX and the significantly decreased performance of catalyst after regeneration have constrained the large-scale industrial application of the technology of methanol to aromatic hydrocarbons.

Therefore, there is a need to develop a method for producing aromatic hydrocarbons from methanol which is advantageous for improving the selectivity to aromatic hydrocarbons and the catalyst life without significant degradation in catalyst performance after regeneration.

SUMMARY OF THE INVENTION

The present invention provides a method for preparing aromatic hydrocarbons from methanol which is advantageous for improving the selectivity to aromatic hydrocarbons and the catalyst life without significant degradation in catalyst performance after regeneration. The effect of this method is mainly achieved by carbon monoxide and an acidic ZSM-5 molecular sieve containing no metal additive as a catalyst.

Specifically, the method for preparing aromatic hydrocarbons provided by the present invention comprises passing methanol and carbon monoxide through a reactor loaded with an acidic ZSM-5 molecular sieve catalyst containing no metal additive, to prepare the aromatic hydrocarbons under reaction conditions.

In a specific embodiment, the molar ratio of the methanol to the carbon monoxide is less than or equal to 1:1.

In a specific embodiment, the molar ratio of the methanol to the carbon monoxide is less than or equal to 1:20 and greater than or equal to 1:100.

In a specific embodiment, the acidic ZSM-5 molecular sieve is a hydrogen-type ZSM-5 molecular sieve.

In a specific embodiment, the atomic ratio of silicon to aluminum in the acidic ZSM-5 molecular sieve is Si/Al=3-200.

In a specific embodiment, the atomic ratio of silicon to aluminum in the acidic ZSM-5 molecular sieve is Si/Al=10-40.

In a specific embodiment, the acidic ZSM-5 molecular sieve is a hydrogen-type ZSM-5 molecular sieve that has not been impregnated with a metal additive, ion exchanged, or physically mixed.

In a specific embodiment, the acidic ZSM-5 molecular sieve comprises at least one selected from the group consisting of a micron stmcture, a nanostmcture, a microporous stmcture and a mesoporous-microporous structure.

In a specific embodiment, the reaction conditions are specially: the reaction temperature is in a range from 350 to 550, the reaction pressure is in a range from 0.5 MPa to 10.0 MPa, and the mass space velocity of methanol is in a range from 0.01 $h^{-1}$ to 20 $h^{-1}$.

In a specific embodiment, the reaction temperature is in a range from 390 to 480, the reaction pressure is in a range from 3 MPa to 7 MPa, and the mass space velocity of methanol is in a range from 0.3 $h^{-1}$ to 3.0 $h^{-1}$.

In a specific embodiment, the reactor is a fixed bed reactor, a moving bed reactor or a fluidized bed reactor for conducting a continuous reaction.

In a specific embodiment, the reactor is a fixed bed reactor.

The reactor is one or more fixed bed reactors. A form of continuous reaction may be taken. The fixed bed reactor may be one or more. When a plurality of the fixed bed reactors are employed, the reactors may be connected in series, in parallel, or in a form of a combination thereof.

The beneficial effects that can be realized by the present invention include:

1) Comparing the method provided by the present invention with the prior art, the selectivity to aromatic hydrocarbons, especially BTX may be improved and stabilized while the single-pass life of the catalyst may be prolonged by adding carbon monoxide in methanol aromatization reaction.

2) Comparing the method provided by the present invention with the prior art, the catalyst deactivated during aromatization of methanol under a carbon monoxide atmosphere has no significant decrease in performance after repeated regenerations.

3) Comparing the method provided by the present invention with the prior art, the step of adding a metal additive is omitted in the preparation process of catalyst, which simplifies the process.

4) Comparing the method provided by the present invention with the prior art, there is no need to add a metal additive to the catalyst, which reduces the cost greatly and facilitates the environmental protection.

DETAILED DESCRIPTION OF THE EMBODIMENT

The present invention will be described in detail below with reference to examples, but the present invention is not limited to these examples.

The raw materials in the examples of the present invention are all commercially purchased, unless otherwise stated.

The analytical methods and the calculation methods for conversion rate and selectivity in the examples are as follows:

Automated analysis is performed using an Agilent 7890 gas chromatograph equipped with a gas autosampler, a TCD detector connected to a TDX-1 packed column and a FID detector connected to a FFAP capillary column.

In some examples of the present invention, both the conversion rate and the selectivity are calculated based on the mole number of carbon:

The conversion rate of methanol=[(mole number of carbon in methanol in the feed)−(mole number of carbon in methanol in the discharge)]÷(mole number of carbon in methanol in the feed)×100%

The selectivity to liquid hydrocarbons (hydrocarbons containing 5 carbons or more)=(mole number of carbon in liquid hydrocarbons in the discharge)÷(mole number of carbon in all products in the discharge)×100%

The selectivity to aromatic hydrocarbons=(mole number of carbon in aromatic hydrocarbons in the discharge)÷(mole number of carbon in all products in the discharge)×100%

The selectivity to BTX=(mole number of carbon in BTX in the discharge)÷(mole number of carbon in all products in the discharge)×100%

Example 1

10 g hydrogen-type ZSM-5 molecular sieve with Si/Al=19 (atomic ratio) (purchased from Catalyst Factory of Nankai University), abbreviated as HZSM-5 (19), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=350, reaction pressure (P)=0.5 MPa, mass space velocity of methanol (WHSV)=0.01 $h^{-1}$, carbon monoxide:methanol (CO:MeOH)=1:1. After the reaction is stabilized, the product is analyzed by gas chromatography, and the reaction results are shown in Table 1.

Example 2

10 g hydrogen-type ZSM-5 molecular sieve with Si/Al=200 (atomic ratio) (purchased from Catalyst Factory of Nankai University), abbreviated as HZSM-5 (200), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=550, reaction pressure (P)=10 MPa, mass space velocity of methanol (WHSV)=20 $h^{-1}$, carbon monoxide:methanol (CO:MeOH)=100:1. After the reaction is stabilized, the product is analyzed by gas chromatography, and the reaction results are shown in Table 1.

Example 3

10 g hydrogen-type ZSM-5 molecular sieve with Si/Al=4 (atomic ratio) (purchased from Shanghai Zhuoyue company), abbreviated as HZSM-5 (4), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=450, reaction pressure (P)=5 MPa, mass space velocity of methanol (WHSV)=2 $h^{-1}$, carbon monoxide:methanol (CO:MeOH)=40:1. After the reaction is stabilized, the product is analyzed by gas chromatography, and the reaction results are shown in Table 1.

Example 4

10 g hydrogen-type ZSM-5 molecular sieve with Si/Al=70 (atomic ratio) (purchased from Shanghai Zhuoyue company), abbreviated as HZSM-5 (70), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=400, reaction pressure (P)=3 MPa, mass space velocity of methanol (WHSV)=1 $h^{-1}$, carbon monoxide:methanol (CO:MeOH)=20:1. After the reaction is stabilized, the product is analyzed by gas chromatography, and the reaction results are shown in Table 1.

Example 5

10 g hydrogen-type ZSM-5 molecular sieve with Si/Al=40 (atomic ratio) (purchased from Shanghai Zhuoyue company), abbreviated as HZSM-5 (40), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=400, reaction pressure (P)=3 MPa, mass space velocity of methanol (WHSV)=1 $h^{-1}$, carbon monoxide:methanol (CO:MeOH)=20:1. After the reaction is stabilized, the product is analyzed by gas chromatography, and the reaction results are shown in Table 1.

Example 6

10 g hydrogen-type ZSM-5 molecular sieve with Si/Al=25 (atomic ratio) (purchased from AOKE company), abbreviated as HZSM-5 (25), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=400, reaction pressure (P)=3 MPa, mass space velocity of methanol (WHSV)=1 h$^{-1}$, carbon monoxide:methanol (CO:MeOH)=20:1. After the reaction is stabilized, the product is analyzed by gas chromatography, and the reaction results are shown in Table 1.

Example 7

10 g hydrogen-type ZSM-5 molecular sieve with Si/Al=25 (atomic ratio) (purchased from AOKE company), abbreviated as HZSM-5 (25), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=390, reaction pressure (P)=3 MPa, mass space velocity of methanol (WHSV)=0.3 h$^{-1}$, carbon monoxide:methanol (CO:MeOH)=20:1. After the reaction is stabilized, the product is analyzed by gas chromatography, and the reaction results are shown in Table 1.

Example 8

10 g hydrogen-type ZSM-5 molecular sieve with Si/Al=25 (atomic ratio) (purchased from AOKE company), abbreviated as HZSM-5 (25), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=480, reaction pressure (P)=7 MPa, mass space velocity of methanol (WHSV)=3 h$^{-1}$, carbon monoxide:methanol (CO:MeOH)=100:1. After the reaction is stabilized, the product is analyzed by gas chromatography, and the reaction results are shown in Table 1.

Example 9

10 g hydrogen-type ZSM-5 molecular sieve with Si/Al=30 (atomic ratio) (purchased from Catalyst Factory of Nankai University), abbreviated as HZSM-5 (30), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=400, reaction pressure (P)=3 MPa, mass space velocity of methanol (WHSV)=1 h$^{-1}$, carbon monoxide:methanol (CO:MeOH)=20:1. After the reaction is stabilized, the product is analyzed by gas chromatography, and the reaction results are shown in Table 1.

Comparative Example 1

10 g hydrogen-type ZSM-5 molecular sieve with Si/Al=30 (atomic ratio) (purchased from Catalyst Factory of Nankai University), abbreviated as HZSM-5 (30), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=400, reaction pressure (P)=3 MPa, mass space velocity of methanol (WHSV)=1 h$^{-1}$, nitrogen:methanol (N$_2$:MeOH)=20:1. After the reaction is stabilized, the product is analyzed by gas chromatography, and the reaction results are shown in Table 1.

Comparative Example 2

10 g hydrogen-type ZSM-5 molecular sieve with Si/Al=30 (atomic ratio) (purchased from Catalyst Factory of Nankai University), abbreviated as HZSM-5 (30), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=400, reaction pressure (P)=0.1 MPa, mass space velocity of methanol (WHSV)=1 h$^{-1}$, nitrogen:methanol (N$_2$:MeOH)=20:1. After the reaction is stabilized, the product is analyzed by gas chromatography, and the reaction results are shown in Table 1.

Comparative Example 3

10 g hydrogen-type ZSM-5 molecular sieve with Si/Al=30 (atomic ratio) (purchased from Catalyst Factory of Nankai University), abbreviated as HZSM-5 (30), is tabletted and sieved to obtain particles of 20-40 mesh, which are then filled into a stainless steel reaction tube with an inner diameter of 16 mm, and activated at 550 for 4 hours with nitrogen of 100 ml/min. The reaction is carried out under the following conditions: reaction temperature (T)=400, reaction pressure (P)=3 MPa, mass space velocity of methanol (WHSV)=1 h$^{-1}$, and no other carrier gas is present. After the reaction is stabilized, the product is analyzed by gas chromatography, and the reaction results are shown in Table 1.

TABLE 1

Catalytic reaction results in Examples 1-7 and Comparative examples 1-3

| Example/ Comparative example | Catalyst | Reaction condition | Reaction time (h) | Conversion rate of methanol (%) | Selectivity to liquid hydrocarbons (%) | Selectivity to aromatic hydrocarbons (%) | Selectivity to BTX (%) |
|---|---|---|---|---|---|---|---|
| Example 1 | HZSM-5 (19) | T = 350 □; P = 0.5 MPa; WHSV = 0.01 h$^{-1}$; CO:MeOH = 1:1 | 5 | 100 | 74.3 | 68.9 | 63.4 |
| Example 2 | HZSM-5 (200) | T = 550 □; P = 10 MPa; WHSV = 20 h$^{-1}$; CO:MeOH = 100:1 | 5 | 100 | 76.8 | 70.6 | 65.8 |

TABLE 1-continued

Catalytic reaction results in Examples 1-7 and Comparative examples 1-3

| Example/ Comparative example | Catalyst | Reaction condition | Reaction time (h) | Conversion rate of methanol (%) | Selectivity to liquid hydrocarbons (%) | Selectivity to aromatic hydrocarbons (%) | Selectivity to BTX (%) |
|---|---|---|---|---|---|---|---|
| Example 3 | HZSM-5 (4) | T = 450 □; P = 5 MPa; WHSV = 2 h⁻¹; CO:MeOH = 40:1 | 5 | 100 | 80.0 | 72.3 | 66.6 |
| Example 4 | HZSM-5 (70) | T = 400 □; P = 3 MPa; WHSV = 1 h⁻¹; CO:MeOH = 20:1 | 5 | 100 | 82.9 | 74.8 | 70.8 |
| Example 5 | HZSM-5 (40) | T = 400 □; P = 3 MPa; WHSV = 1 h⁻¹; CO:MeOH = 20:1 | 5 | 100 | 80.3 | 71.7 | 68.2 |
| Example 6 | HZSM-5 (25) | T = 400 □; P = 3 MPa; WHSV = 1 h⁻¹; CO:MeOH = 20:1 | 5 | 100 | 82.4 | 73.4 | 69.9 |
| Example 7 | HZSM-5 (25) | T = 390 □; P = 3 MPa; WHSV = 0.3 h⁻¹; CO:MeOH = 20:1 | 5 | 100 | 79.8 | 71.8 | 70.0 |
| Example 8 | HZSM-5 (25) | T = 480 □; P = 7 MPa; WHSV = 3.0 h⁻¹; CO:MeOH = 100:1 | 5 | 100 | 78.5 | 72.2 | 71.6 |
| Example 9 | HZSM-5 (30) | T = 400 □; P = 3 MPa; WHSV = 1 h⁻¹; CO:MeOH = 20:1 | 5 | 100 | 82.5 | 76.6 | 71.9 |
| | | | 20 | 100 | 82.4 | 76.6 | 71.8 |
| | | | 300 | 100 | 77.3 | 73.2 | 66.4 |
| Comparative example 1 | HZSM-5 (30) | T = 400 □; P = 3 MPa; WHSV = 1 h⁻¹; N₂:MeOH = 20:1 | 5 | 100 | 57.3 | 30.5 | 24.4 |
| | | | 20 | 100 | 48.6 | 25.4 | 20.0 |
| | | | 100 | 50.8 | 15.4 | 3.1 | 1.5 |
| Comparative example 2 | HZSM-5 (30) | T = 400 □; P = 0.1 MPa; WHSV = 1 h⁻¹; N₂:MeOH = 20:1 | 5 | 100 | 60.7 | 36.7 | 30.9 |
| | | | 20 | 100 | 41.0 | 28.9 | 22.2 |
| | | | 100 | 37.8 | 10.9 | 2.5 | 1.1 |
| Comparative example 3 | HZSM-5 (30) | T = 400 □; P = 3 MPa; WHSV = 1 h⁻¹; | 5 | 100 | 56.7 | 35.5 | 31.7 |
| | | | 20 | 100 | 44.3 | 27.9 | 21.2 |
| | | | 100 | 45.1 | 14.8 | 3.7 | 2.1 |

Regeneration Performance Test of Catalyst

Example 10

The deactivated catalyst in Example 9 is treated at 550 for 10 hours with a gas mixture comprising 2% oxygen and 98% nitrogen by volume fraction, so that the catalyst is regenerated for one cycle and used in the reaction carried out under the conditions of Example 9. Five cycles of regeneration are conducted in the same manner, and the catalytic activity data after 20 hours of reaction for each cycle is selected for comparison. The results are shown in Table 2.

Comparative Example 4

The HZSM-5 (30) in Example 9 is impregnated with a zinc nitrate solution by an equal-volume method, dried and calcined at 550 to obtain an acidic ZSM-5 molecular sieve with a zinc content of 2%, abbreviated as Zn/HZSM-5 (30). The catalyst is used in the reaction carried out under the conditions of Example 9, and is regenerated under the conditions of Example 10, so that the catalyst is regenerated for one cycle and used in the reaction carried out under the conditions of Example 9. Five cycles of regeneration are conducted in the same manner, and the catalytic activity data after 20 hours of reaction for each cycle is selected for comparison. The results are shown in Table 2.

TABLE 2

Catalytic reaction results in Example 10 and Comparative example 4

| Example/ Comparative example | Catalyst | Fresh/Cycle times of regeneration | Conversion rate of methanol (%) | Selectivity to liquid hydrocarbons (%) | Selectivity to aromatic hydrocarbons (%) | Selectivity to BTX (%) | Life (h) |
|---|---|---|---|---|---|---|---|
| Example 10 | HZSM-5 (30) | Fresh | 100 | 82.4 | 76.6 | 71.8 | 1200 |
| | | Regeneration First cycle | 100 | 83.3 | 75.8 | 72.0 | 1300 |

TABLE 2-continued

Catalytic reaction results in Example 10 and Comparative example 4

| Example/Comparative example | Catalyst | Fresh/Cycle times of regeneration | Conversion rate of methanol (%) | Selectivity to liquid hydrocarbons (%) | Selectivity to aromatic hydrocarbons (%) | Selectivity to BTX (%) | Life (h) |
|---|---|---|---|---|---|---|---|
| | | Regeneration Second cycle | 100 | 82.9 | 76.1 | 71.9 | 1150 |
| | | Regeneration Third cycle | 100 | 83.0 | 75.9 | 71.8 | 1250 |
| | | Regeneration Fourth cycle | 100 | 82.8 | 75.6 | 71.3 | 1200 |
| | | Regeneration Fifth cycle | 100 | 83.2 | 76.0 | 72.1 | 1180 |
| Comparative example 4 | Zn/HZSM-5 (30) | Fresh | 100 | 80.0 | 75.8 | 68.9 | 500 |
| | | Regeneration First cycle | 100 | 75.6 | 70.2 | 60.6 | 350 |
| | | Regeneration Second cycle | 100 | 70.5 | 62.9 | 54.7 | 280 |
| | | Regeneration Third cycle | 100 | 60.2 | 50.3 | 41.9 | 190 |
| | | Regeneration Fourth cycle | 100 | 58.8 | 48.7 | 37.9 | 150 |
| | | Regeneration Fifth cycle | 100 | 53.9 | 44.6 | 32.1 | 120 |

It can be seen from Table 2 that the acidic ZSM-5 molecular sieve containing no metal additive after regeneration has a significant improvement in the selectivity to aromatic hydrocarbons and BTX and the catalyst life.

The above are only a few embodiments of the present application, and are not intended to limit the present application in any form. Although the present application is disclosed by the preferred embodiments as above, they are however not used to limit the present application. A slight change or modification utilizing the technical content disclosed above made by the person skilled in art, without departing from the technical solution of the present application, is equivalent to the equivalent embodiment, and falls within the scope of the technical solution.

What is claimed is:

1. A method for preparing aromatic hydrocarbons, wherein the method comprises passing methanol and carbon monoxide through a reactor loaded with an acidic ZSM-5 molecular sieve catalyst containing no metal additive, to prepare the aromatic hydrocarbons under reaction conditions, wherein the acidic ZSM-5 molecular sieve has not been impregnated, ion exchanged, or physically mixed with a metal additive, wherein the acidic ZSM-5 molecular sieve is a hydrogen-type ZSM-5 molecular sieve, and wherein a molar ratio of the methanol to the carbon monoxide is less than or equal to 1:20, and greater than or equal to 1:100.

2. The method according to claim 1, wherein an atomic ratio of silicon to aluminum (Si/Al) in the acidic ZSM-5 molecular sieve is in a range of 3-200.

3. The method according to claim 2, wherein the atomic ratio of silicon to aluminum (Si/Al) in the acidic ZSM-5 molecular sieve is in a range of 10-40.

4. The method according to claim 1, wherein the reaction conditions include: a reaction temperature in a range from 350° C. to 550° C., a reaction pressure in a range from 0.5 MPa to 10.0 MPa, and a mass space velocity of methanol in a range from 0.01 $h^{-1}$ to 20 $h^{-1}$.

5. The method according to claim 4, wherein the reaction temperature is in a range from 390° C. to 480° C., the reaction pressure is in a range from 3 MPa to 7 MPa, and the mass space velocity of methanol is in a range from 0.3 $h^{-1}$ to 3.0 $h^{-1}$.

6. The method according to claim 1, wherein the reactor is a fixed bed reactor, a moving bed reactor or a fluidized bed reactor for conducting a continuous reaction.

7. The method according to claim 6, wherein the reactor is a fixed bed reactor.

\* \* \* \* \*